United States Patent [19]

Falciani et al.

[11] 4,310,460

[45] Jan. 12, 1982

[54] PROCESS FOR THE PRODUCTION OF 6-D-α-AMINO-P-HYDROXY-PHENYLACETAMIDO PENICILLANIC ACID

[75] Inventors: Marco Falciani; Renato Broggi, both of Milan, Italy

[73] Assignee: Dobfar S.p.A., Milan, Italy

[21] Appl. No.: 133,442

[22] Filed: Mar. 24, 1980

[30] Foreign Application Priority Data

Nov. 2, 1979 [IT]   Italy ................................ 27013 A/79

[51] Int. Cl.³ .......................................... C07D 499/12
[52] U.S. Cl. ..................................... 260/239.1; 560/39
[58] Field of Search ....................................... 260/239.1

[56]         References Cited
        U.S. PATENT DOCUMENTS
    3,980,637  9/1976  Grossman et al. ............... 260/239.1
    4,127,571 11/1978  Broggi et al. .................... 260/239.1

FOREIGN PATENT DOCUMENTS 737848 8/1969 Belgium .
2520647 11/1975 Fed. Rep. of Germany .
978178 12/1964 United Kingdom .
1241844 8/1971 United Kingdom .

Primary Examiner—Natalie Trousof
Assistant Examiner—Vera C. Clarke
Attorney, Agent, or Firm—Oblon, Fisher, Spivak, McClelland & Maier

[57]         ABSTRACT

Process for the production of 6-D-α-amino-p-hydroxyphenylacetamido penicillanic acid which is a potent antibiotic also known generically as amoxicillin. According to the process there is reacted a boron derivative of 6-APA with an acylating agent derived from the D(-)-p-hydroxyphenylglycine, in dimethylformamide or in dimethylsulfoxide in admixture with methylene chloride or chloroform, hydrolyzing and then removing the enaminic group.

5 Claims, No Drawings

PROCESS FOR THE PRODUCTION OF 6-D-α-AMINO-P-HYDROXY-PHENYLACETAMIDO PENICILLANIC ACID

The present invention relates to a process for the preparation of 6-D-α-amino-p-hydroxyphenylacetamido penicillanic acid, which is an antibiotic generically known with the name of amoxicillin.

The amoxicillin is a product already well known, described in British Pat. No. 978,178. According to said patent, the amoxicillin is prepared by the synthesis of the 6-aminopenicillanic acid (commonly known as 6-APA) with the mixed anhydride formed by the reaction of ethyl chloroformate with O,N-dibenzyloxycarbonyl-p-hydroxy phenylglycine and subsequent removal of the protective groups by catalytic hydrogenation.

There are known numerous other processes, which are of little interest from the economic point of view, relating to the production of the amoxicillin.

Belgian Pat. No. 737,848 describes the synthesis of the amoxicillin from 6-APA and the mixed anhydride obtained by a Dane salt of the p-hydroxyphenylglycine and ethyl chloroformate. The intermediate products which are formed in this reaction are isolated; it is not possible to calculate the total yields of amoxicillin. An analogous process is described in German Patent Application DOS No. 2,520,647 where, thanks to the use of a catalyst, such as the dimethylacetamide hydrochloride, there are obtained yields up to 78%. No mention is made, however, with regard to the purity of the final product.

British Pat. No. 1,241,844 illustrates a process in which the aminic group of the p-hydroxyphenylglycine is protected by means of the carbobenzyloxy group and the use of the p-hydroxyphenylglycine chloride hydrochloride by the reaction with 6-APA in an aqueous phase; the yields are not disclosed.

According to U.S. Pat. No. 3,980,637 there are utilized, on the other hand, the p-hydroxyphenylglycine chloride hydrochloride with the mono- and disilyl derivative of 6-APA in an organic solvent. The yield are high but the amoxicillin thus obtained must be purified with resins because of the use of dimethylaniline.

The process described in U.S. Pat. No. 4,127,571 also uses the p-hydroxyphenylglycine chloride hydrochloride with the reaction with the O,N-disubstituted 6-APA with cyclic derivatives of boron. European Pat. No. 1,133 describes a method in which there is reacted a silyl derivative of 6-APA with a mixed anhydride of a Dane salt of the p-hydroxyphenylglycine with the help of a mixture of solvents and cosolvents. As cosolvents there are indicated dimethylformamide, sulfolane, tetrahydrofuran, N-methylpyrrolidone, 1,4-dioxane, acetonitrile, dimethylacetamide and tetramethylurea. The final product (amoxicillin) obtained by the method of the European Pat. No. 1,133 presents impurities which result from the use of the silyl derivative of the 6-APA (such as hexamethyldisiloxane) which are very difficult to eliminate, due to their insolubility in water.

The present applicants, in order to overcome the above mentioned inconvenients, have tried to substitute the silyl derivative of the 6-APA with other derivatives of the 6-APA, but without obtaining appreciable results. Among these derivatives of the 6-APA, applicants have used the boron derivatives of 6-APA (described in U.S. Pat. No. 4,127,571 and in Italian Patent Application No. 26,865 A/79), but the yields obtained did not prove to be of any industrial interest. It has now been surprisingly found that, if instead of using the mixture of solvents and cosolvents described in the European patent, one reacts a boron derivative of the 6-APA with a mixed anhydride of a Dane salt of the p-hydroxyphenylglycine prepared in a solvent selected from the group consisting of dimethylformamide, used alone, and dimethylsulfoxide in admixture with methylene chloride or chloroform, there are obtained high yields of the final product which may be isolated in a highly pure state.

The present invention thus relates to a process for the production of 6-D-α-amino-p-hydroxyphenylacetamido penicillanic acid, characterized by the fact that there are reacted a boron derivative of 6-APA of the formula

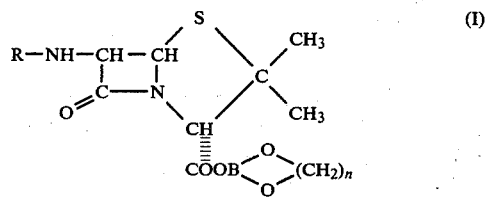

wherein
R is —H or

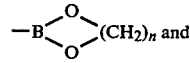

n is 2 or 3, with an at least equimolar quantity of an acylating agent derived from the D(-)-p-hydroxyphenylglycine of formula (II):

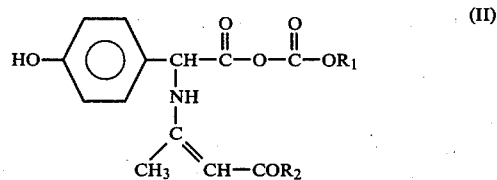

where
$R_1$ is an alkyl radical such as methyl, ethyl and isobutyl and
$R_2$ is an alkoxy radical such as methoxy and ethoxy, in a solvent selected from the group consisting of dimethylformamide alone and of dimethylsulfoxide mixed with mehylene chloride or chloroform,
the reaction mixture is hydrolyzed with water obtaining two phases, the enaminic group is removed by lowering the pH of the reaction mixtures to 0.8-1.8 by means of the addition of an aqueous solution of an acid, from the aqueous solution containing amoxicillin hydrochloride there being isolated amoxicillin trihydrate by means of known techniques. The compounds of formula (I) are prepared according to the processes described in U.S. Pat. No. 4,127,571 and in Italian Patent Application No. 26,865 A/79.

The derivatives of the p-hydrophenylglycine of formula (II) are known per se and are described in Belgian Pat. No. 737,848. Preferably they are prepared according to the method described in European Pat. No. 1,133, according to which they are prepared by the reaction of the corresponding Dane salt of the D(-)-p-hydroxyphenylglycine (selected from that formed by condensation of the p-hydroxy-phenylclycine with methyl acetoacetate or with ethyl acetoacetate) with a chloroformate selected from the group consisting of ethyl chloroformate, methyl chloroformate and isobutyl chloroformate in the presence of N-methylmorpholine or N,N-dimethylbenzylamine as catalysts.

The removal of the protective enaminic group, at the end of the reaction, is effected by using hydrochloric acid of a concentration of about 37%.

The phases are separated and the aqueous phase containing the amoxicillin chlorohydrate in solution is purified. From the purified aqueous phase, the amoxicillin trihydrate is isolated by precipitation by the addition of an inorganic base, such as dilute ammonium hydroxide, dilute sodium hydroxide or dilute potassium hydroxide, until the pH of the mixture reaches a value of 4.7–5.2. The resulting product is then filtered, washed and air dried.

One of the advantages obtained by the process of the present invention is constituted by the high degree of purity of the product obtained; in fact the products deriving from the hydrolysis of the boron esters are extremely soluble in water.

Another advantage resides in the excellent yields obtained with the process of the present invention; in fact there is obtained a conversion of amoxicillin present in solution of about 97% and a yield of amoxicillin, after isolation, of about 84%, yields which are thus higher than those obtained with the known processes.

In addition, with respect to the other patents which use p-hydroxyphenylglycine chloride hydrochloride, which is very expensive and unstable (it does not permit long periods of storage) the process of the present invention has the advantage of utilizing the Dane salts of p-hydroxyphenylglycine which are stable and which can be stored for extended periods.

In order to render clearer the teachings of the present process, there will now be described some illustrative operative examples.

EXAMPLE 1

(a) Preparation of an ethoxy carbonyl D-α-(1-carbomethoxypropenyl)-amino-p-hydroxyphenyl acetate (of formula II).

In a 2 l round bottom flask there are charged 37.4 g (0.123 mols) of the methyl potassium Dane salt of p-hydroxyphenylglycine in 220 ml of $CH_2Cl_2$(K.F. 0.0015%); there are then added 26 ml of dimethylsulfoxide (DMSO) and, with stirring, the mixture is cooled to −40° C. There are then added 13.9 g of ethyl chloroformate and 0.35 ml of N-methylmorpholine.

The exotherm of the reaction is maintained within −35° C. and the mixture is allowed to react at −35° C. for 2 hours.

The reaction mixture is cooled to −50° C.

(b) Preparation of a suspension of 6-APA boron ester in a solvent.

In a round bottom flask there are placed 266 ml of anhydrous $CH_2Cl_2$ (K.F. 0.0015%). The solvent is cooled to −50° C. and there are added, at this temperature, 80 g of product obtained according to the method described in Italian Patent Application No. 26,865 A/79, containing 6-APA intermediate equal to 26.6 g of 6-APA base titered by means of HPLC; it is noted on I.R. analysis the disappearance of the carboxylic band at 1600 nm.

(c) Preparation of amoxicillin

The mixture (b), cooled to −50° C., is added as rapidly as possible to the suspension of the mixed anhydride obtained in (a); the exotherm is maintained within −35° C. and the mixture is maintained at this temperature for 1 hour. One ml of reaction mixture is withdrawn and is hydrolyzed with a solution of 4 ml $H_2O$ and 1 ml acetone; 30-50-10 μl of the solution are placed on silica gel plate GF 254 with comparison of amoxicillin and 6-APA.

Elution is carried out in $CH_3$-CN 20 ml:$H_2O$ 3.5 ml:HCOOH 2 ml.

The plate is developed with ninhydrin and there noted the appearance of a spot of amoxicillin and the absence of unreacted 6-APA. At the end of the condensation there is added a mixture of 133 ml $H_2O$ and 40 ml acetone; then, at 0° C., there is added dropwise an HCl solution (37% concentration) to hydrolyze the enamine to a constant pH in the range of 1–1.3; after 1 hour at a constant pH the two phases separate. The organic phase is extracted again at a pH of 1–1.3 with a mixture of 133 ml $H_2O$ and 40 ml acetone.

The combined aqueous phases containing amoxicillin are filtered and the content of amoxicillin is determined by HPLC and microbiologically. It results equal to 95% of theoretical. By crystallization by means of known techniques there are obtained 42.3 g of amoxicillin trihydrate having a microbiological purity of 847 mcg/mg, with a yield of 82%.

EXAMPLE 2

(a) Preparation of ethoxy carbonyl D-α-(1-carbomethoxypropenyl)-amino-p-hydroxyphenyl acetate (of formula II).

In a 2 l round bottom flask there are charged 42.2 g (0.1388mols) of the methyl potassium Dane salt of the p-hydroxyphenylglycine in 250 ml of anhydrous $CH_2Cl_2$ (K.F. 0.0015%); there are then added 30 ml of DMSO and, with stirring, the mixture is cooled to −40° C. There are then added 15.7 g (0.144 mols) of ethyl chloroformate and 0.4 ml of N-methylmorpholine.

The exotherm is contained within −35° C. and the reaction mixture is allowed to react at −35° C. for 2 hours. The reaction mixture is then cooled to −50° C.

(b) Preparation of the boron ester of 6-APA (of formula I)

In a round bottom flask there are introduced 300 ml of anhydrous $CH_2Cl_2$ (K.F. 0.0015%); there are then added 30 g (0.1388 mols) of 6-APA at ambient temperature, and then 28.05 g (0.277 mols) of TEA and the mixture is stirred at ambient temperature for 1 hour. The mixture is then cooled to −50° C. and, over 30′, there is added dropwise a solution of methylene chloride containing 29.49 g of ethyl chloroboronate (256 ml containing 11.52 g/100 ml). At the end of the addition, the mixture is left at −50° C. for 2 hours. On a small aliquot there is effected the I.R. control which shows the disappearance of the carboxy band at 1600 nm.

(c) Preparation of amoxicillin

The reaction mixture obtained in (b), cooled to −50° C., is added as fast as possible to the suspension of the mixed anhydride prepared in (a). The exotherm is maintained within −35° C. and the reaction mixture is maintained at this temperature for 1 hour. There is then effected a TLC following the technique described in Example 1 (c), detecting the presence of amoxicillin and the absence of unreacted 6-APA. At the end of the condensation there is added a mixture precooled to 0°

C. of 150 ml of H₂O and 45 ml of acetone and at 0° C. the enamine is hydrolyzed by the addition of 37% HCl down to a constant pH of 1–1.3. The mixture is then allowed to stir for 1 hour at a constant pH.

The phases are separated and the organic phase is extracted again at pH 1–1.3 with a mixture of 150 ml H₂O and 45 ml acetone. The aqueous phases are combined and filtered. The exact volume is measured and on a small aliquot thereof there is carried out an HPLC titration. There are present in solution 56.7 g, equal to a theoretical yield of 97.5%, value which is also confirmed microbiologically. To the rich waters, cooled to 0° C., there is added a solution of 10% NaOH to adjust the pH to 5–5.2. Seeding is effected to begin the crystallization step and, once crystallization is completed, the mixture is left for 5 hours under stirring conditions. The precipitate is removed by filtration, washed with 100 ml H₂O:acetone=1:1, then with acetone. After vacuum drying there are obtained 48.3 g, equal to a theoretical yield of 83%, with a microbiological purity of 845 mcg/mg. $[\alpha]_D = +303°$ on dry basis.

Preparing the mixed anhydride of the Dane salt (formula II) described un part (a) using only CH₂Cl₂ there is not achieved the formation of the mixed anhydride.

It is not possible to conduct such reaction in DMSO alone since it, at a temperature of about 18° C., solidifies and it is thus impossible to achieve the low temperatures necessary for the synthesis. For the synthesis it is necessary to have a temperature of −50° C., to achieve this it is thus necessary to mix the DMSO with a solvent which would prevent the solidification thereof.

Useful for this scope have been found to be methylene chloride and chloroform.

EXAMPLE 3

The same process indicated in Example 2 is used, with the exception that in the phase (a) there are used 20 ml of DMSO instead of 30 ml. The final product is crystallized from the final aqueous solution by cooling it to 0° C. and bringing the pH to 5–5.2 with a 10% solution of KOH. Crystallization is brought about by seeding with 0.1 g of product and the solution is allowed to crystallize at 0° C. for 5 hours. The result solid is filtered, washed with 100 ml of water:acetone (1:1), then with 50 ml of acetone. Then the residue is dried at 40° C. in an air oven obtaining 48.8 g, equal to 84% of the theoretical yield, of amoxicillin, having a purity of 98.8%, titrated mercuriometrically, $[\alpha]_D = +302°$ on dry basis, K.F. 13.8%.

EXAMPLE 4

There is used the same process used in Example 2, except that in the phase (a) there are used 36 ml of DMSO instead of 30 ml. The product is isolated by crystallization obtaining 46.2 of amoxicillin, equal to a yield based on the theoretical yield of 79.5%, with a purity, measured microbiologically, of 846 mcg/mg, K.F. 14.1%. $[\alpha]_D = +300°$ on dry basis.

EXAMPLE 5

(a) Preparation of 2-ethoxy-carbonyl-α-(1-carbomethoxypropenyl)-amino-p-hydroxyphenyl acetate (of formula II)

In a 2 l round bottom flask there are charged 44.31 g (0.145 mols) of the methyl potassium Dane salt of p-hydroxyphenylglycine in 250 ml of anhydrous methylene chloride (K.F. 0.0015%), there are then added 30 ml of DMSO and, with stirring, at $-\cong°$ C. there are added 16.5 g (0.152 mols) of ethyl chloroformate and 0.4 ml of N-methylmorpholine. The exotherm is maintained within −20° C. The reaction mixture is the maintained at −20° C. for 1 hour and then cooled to −50° C.

(b) Preparation of 6-APA boron ester (of formula I)

There are used the same process and the same stochiometric quantities used in Example 2, part (b).

(c) Preparation of amoxicillin trihydrate

There is used the same process indicated in Example 2, part (c).

The rich waters are titrated by means of HPLC and microbiologically and there are obtained in solution 56.1 g, equal to 96.5% of the theoretical yield. Upon crystallization, there are obtained 47.7 g of amoxicillin, equal to 82% of the theory, with a purity of 98.8%, determined by HPLC and microbiologically, of 851 mcg/mg, K.F. 13.8%, $[\alpha]_D = +302°$ on dry basis.

EXAMPLE 6

(a) Preparation of the ethoxy carbonyl D-α-(1-carbomethoxypropenyl)-amino-p-hydroxy phenylacetate (formula II)

In a round bottom flask (2 l) there are charged 46.4 g (0.152 mols) of methyl potassium Dane salt of p-hydroxyphenylglycine in 250 ml of anhydrous methylene chloride (K.F. 0.0015%); there are then added 30 ml of DMSO and, under agitation, the mixture is cooled to −30° C. There are then added 17.26 g (0.159 mols) of ethyl chloroformate and 0.4 ml of N-methyl-morpholine. The exotherm is maintained within −25° C. and the reaction mixture is maintained at −25° C. for 1 hour. The reaction mixture is then cooled to −50° C.

(b) Preparation of 6-APA boron ester (of formula I)

There is used the same process set forth in Example 2, part (b).

(c) Preparation of amoxicillin trihydrate

There is used the same process set forth in Example 2, part (c). The waters rich in product, titrated in HPLC, are found to contain 56.4 g of amoxicillin, equal to 97% of the theoretical yield. There is isolated amoxicillin trihydrate (47.2 g), equal to 81.5% of the theoretical yield, with a purity measured by known techniques of 98.7%.

EXAMPLE 7

(a) Preparation of the ethoxy carbonyl D-α-(1-carbomethoxy propenyl)amino-p-hydroxy phenyl acetate (of formula II)

In a round bottom flask there are charged 42.2 g (0.1388 mols) of the methyl potassium Dane salt of p-hydroxyphenylglycine in 90 ml of anhydrous dimethylformamide (DMF). The mixture is cooled to −40° C. and there are added 15.7 g of ethyl chloroformate and 0.4 ml of N-methylmorpholine. The exoterm is maintained within −35° C. and the mixture is allowed to react at −35° C. for 2 hours. The reaction mixture is then cooled to −50° C.

(b) Preparation of the 6-APA boron ester (of formula I)

For the preparation of the 6-APA boron ester there were used the same process and quantities described in Example 2, part (b).

(c) Preparation of amoxicillin trihydrate.

To the suspension prepared in (a), cooled to −50° C., there is added as rapidly as possible the reaction mixture prepared in (b). The exotherm is contained within −25° C. and the mixture is maintained at −25° C. for 1 hour. There is then withdrawn 1 ml of suspension which is hydrolyzed with 5 ml of H₂O:acetone (4:1). There is effected a TLC following the technique described in Example 1. With ninhydrin there is detected the presence of amoxicillin and there is verified the absence of unreacted 6-APA. The reaction mixture is treated using the same technique and quantities described in Example 2(c). The solution of the rich waters containing the product titrated by means of HPLC is found to contain 56.4 g of amoxicillin, equal to 97% of theoretical.

From these rich waters there are obtained by crystallization 48.8 g, equal to 83.8% of theoretical, having the following analytical characteristics:

K.F.=13.8%.
$[\alpha]_D = +302°$ on dry basis.
Spectrophotometric titer=98.8% on dry basis
Microbiological titer=851 mcg/mg

EXAMPLE 8

There is used the same process indicated in Example 2 with the exception that in the phase (a) there are used 220 ml of chloroform instead of 250 ml of $CH_2Cl_2$.

The rich waters are cooled to 0° C. There are crystallized 46.8 g of amoxicillin trihydrate, equal to a yield of 80.5% of theoretical.

EXAMPLE 9

(a) Preparation of ethoxy carbonyl D-$\alpha$-(1-carbomethoxy propenyl)amino p-hydroxy phenylacetate (of formula II)

In a 2 l round bottom flask there are charged 250 ml of anhydrous $CH_2Cl_2$ (K.F. 0.0015%) and 44.3 g (0.145 mols) of the methyl potassium Dane salt of p-hydroxyphenylglycine. With stirring, there are added 30 ml of DMSO and the mixture is cooled to $-40°$ C. There are then added 16.5 g (0.151 mols) of ethyl chloroformate and 0.4 ml of N-methylmorpholine. The exotherm is maintained within $-35°$ C. and the mixture is then allowed to react at $-35°$ C. for 2 hours. The reaction mixture is then cooled to $-50°$ C.

(b) Preparation of 6-APA boron ester (of formula I)

In a round bottom reaction flask there are introduced 300 ml of anhydrous $CH_2Cl_2$ (K.F. 0.0015%) and there are then added 30 g (0.1388 mols) of 6-APA and 25.15 g (0.249 mols) of TEA at ambient temperature. The mixture is left at ambient temperature for 1 hour. It is then cooled to $-45°$ C. and, over a period of 30', there is added dropwise a solution of 26.5 g (0.249 mols) of ethylene chloroboronate in methylene chloride (230 ml containing 11.52 g/100 ml).

At the end of the addition the mixture is left for 2 hours at $-45°$ C. On a small aliquot thereof there is effected an I.R. control which shows the disappearance of the carboxy band at 1600 nm.

(c) Preparation of amoxicillin trihydrate

There is followed the same technique and there are used the same quantities described in Example 2, part (c). The rich waters titrated for HPLC containing 55.3 g of amoxicillin trihydrate, equal to 95% of theoretical. By crystallization there are obtained 47.3 g, equal to 81.3% of theoretical, with a purity, measured spectrophotometrically, of 99.2%. K.F. 14.2%

EXAMPLE 10

(a) Preparation of ethoxy carbonyl D-$\alpha$-(1-carbomethoxypropenyl)amino p-hydroxy phenylacetate (of formula II).

It is prepared using the same techniques and quantities described in Example 9, part (a).

(b) Preparation of the 6-APA boron ester (of formula I)

In a round bottom reaction flask there are introduced 300 ml of anhydrous $CH_2Cl_2$ (K.F. 0.0015%) and there are added 30 g (0.1388 mols) of 6-APA and 21 g (0.207 mols) of TEA at ambient temperature. The mixture is maintained at ambient temperature for 1 hour. It is then cooled to $-50°$ C. and, over a period of 30 minutes, there is added dropwise a solution of 22.12 g (0.208 mols) of ethylene chloroborate in methylene chloride (192 ml containing 11.52 g/100 ml). At the end of the addition the mixture is left at $-50°$ C. for 2 hours. The I.R. control shows the disappearance of the carboxy band at 1600 nm.

(c) Preparation of amoxicillin thihydrate

Following the technique and using the quantities described in Example 2, part (c) there is crystallized amoxicillin trihydrate obtaining 44.2 g, equal to 76% of theoretical, with a microbiological purity of 851 mcg/mg and K.F. 13.8%.

EXAMPLE 11

(a) Preparation of ethoxy carbonyl D-$\alpha$-(1-carbomethoxy propenyl)amino-p-hydroxy phenyl acetate (of formula II)

The preparation is carried out using the same technique and quantities described in Example 9, part (a).

(b) Preparation of the 6-APA boron ester (of formula I)

Using the same technique described in Example 2 (b) there is obtained 6-APA boron ester using 30 g (0.1388 mols) of 6-APA, 30.84 g (0.304 mols) of TEA and 32.45 g of ethylene chloroboronate in methylene chloride (281 ml containing 11.52 g/100 ml).

(c) Preparation of amoxicillin trihydrate

Following the same technique and using the same quantities described in Example 2 (c) there are obtained 46.5 g of amoxicillin trihydrate with a yield of 80% of theoretical and with a purity, measured microbiologically, of 852 mcg/mg, K.F. 13.3%, $[\alpha]_D = +300°$ on dry basis.

EXAMPLE 12

(a) Preparation of ethoxy carbonyl D-$\alpha$-(1-carbomethoxy propenyl)amino p-hydroxy phenyl acetate (of formula II)

It is prepared using the same technique and the same quantities described in Example 9 (a).

(b) Preparation of 6-APA boron ester (of formula I)

In the same manner described in Example 2 (b) there is obtained 6-APA boron ester using 30 g (0.1388 mols) of 6-APA, 26.6 g (0.263 mols) of TEA and 26.5 g (0.249 mols) of ethylene chloroboronate in methylene chloride (230 ml containing 11.52 g/100 ml).

(c) Preparation of amoxicillin trihydrate

Following the same technique and using the same quantities described in Example 2 (c) there are obtained 46.8 of amoxicillin trihydrate with a yield of 80.4% of theoretical, with a purity measured spectrophotometrically, of 98.7% and K.F. 14%.

Repeating the same processes described above, but using for the preparation of the product of formula (II) described in the part (a) as solvents, instead of DMSO+$CH_2Cl_2$, mixtures of solvents and cosolvents described in European Pat. No. 1,133, there are obtained much lower yields, in the order of about 40%, with the only exception of the mixture, dimethylformamide and methylene chloride; in this case it is the dimethylformamide which promotes the reaction (see Example 7) since the methylene chloride is an inert solvent.

According to the preceding examples, there is obtained an amoxicillin trihydrate, the analytical characteristics of which are the following:

Appearance: crystalline white powder.
I.R.: positive identification against a standard
Umidity (K.F.): 13.3%
pH (100 mg/ml): 4.9
HPLC titer: 99.5% b.w. (on dry basis)
Amino titer: 99% b.w.
Jodometric titer: 98.8% b.w.
Acid titer: 101%
Spectrophotometric titer: 99.1% b.w.
Specific rotation $[\alpha]_D^{20}$: +303° b.w.
Transmittance (1% HCl 1 N 400 mµ): 85% b.w.
Solvents determined for GLC:
    Dimethylaniline (not detectable)
    Methylene chloride (0.08%)
    Acetone (0.1%)
    Triethylamine (0.03%)
Microbiological titer: 855 mcg/mg
Stability 65°×7 days: 845 mcg/mg
Toxicity: non toxic

What is claimed is:

1. A process for the production of the 6-D-α-amino-p-hydroxyphenylacetamido penicillanic acid, wherein, under anhydrous conditions and at a temperature between −20° C. and −60° C. there is reacted a compound of the formula:

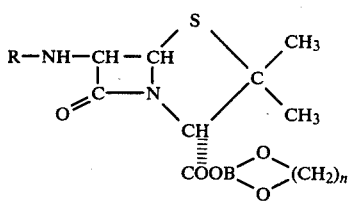
(I)

wherein R is —H or

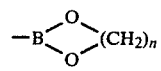

and n is 2 or 3, with a compound of the formula:

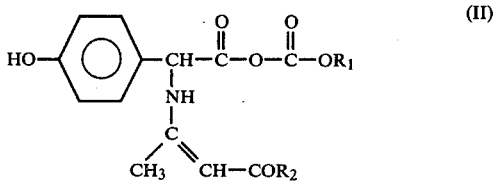
(II)

wherein $R_1$ is an alkyl radical and $R_2$ is an alkoxy radical, in a solvent selected from the group consisting of dimethylformamide alone and of dimethylsulfoxide in admixture with methylene chloride or chloroform, and the resulting reaction mixture is treated as follows:

(a) the mixture is hydrolyzed with water obtaining two phases;
(b) the pH of the reaction mixture is lowered to about 0.8–1.8 by the addition of an aqueous solution of an acid, to remove the anaminic group;
(c) the aqueous phase is separated and treated by known means to convert the amoxicillin chlorohydrate contained therein to amoxicillin trihydrate, and
(d) the resulting product is isolated.

2. A process according to claim 1, wherein the aqueous acid solution is a solution of hydrochloric acid at a concentration of about 37%.

3. A process according to claim 1 wherein the temperature at which the compound of formula (I) is reacted with the compound of formula (II) is about −35° C.

4. A process according to claim 1, wherein $R_1$ is a radical selected from the group consisting of methyl, ethyl and isobutyl.

5. A process according to claim 1, wherein $R_2$ is a radical selected from the group consisting of methoxy and ethoxy.

* * * * *